United States Patent [19]

Fischer et al.

[11] Patent Number: 4,874,709

[45] Date of Patent: Oct. 17, 1989

[54] SOLVENT AND METHOD FOR THE KARL-FISCHER DETERMINATION OF WATER

[75] Inventors: Wolfgang Fischer, Darmstadt; Karl D. Krenn, Pfungstadt, both of Fed. Rep. of Germany

[73] Assignee: Merck Patent Gesellschaft mit Beschränkter Haftung, Darmstadt, Fed. Rep. of Germany

[21] Appl. No.: 217,912

[22] Filed: Jul. 12, 1988

[30] Foreign Application Priority Data

Jul. 13, 1987 [DE] Fed. Rep. of Germany ....... 3723084

[51] Int. Cl.$^4$ ............................................. G01N 33/18
[52] U.S. Cl. ...................................... 436/42; 204/1 T; 436/60
[58] Field of Search .................... 436/42, 60; 204/1 T

[56] References Cited

U.S. PATENT DOCUMENTS

| | | | |
|---|---|---|---|
| 4,416,997 | 11/1983 | Fischer et al. | 436/42 |
| 4,619,900 | 10/1986 | Scholz | 436/42 |
| 4,703,014 | 10/1987 | Fischer et al. | 436/42 |

FOREIGN PATENT DOCUMENTS 1174951 9/1984 Canada .................................. 436/42

*Primary Examiner*—Robert J. Hill, Jr.
*Attorney, Agent, or Firm*—Millen, White & Zelano

[57] ABSTRACT

The invention relates to a solvent for the Karl-Fischer determination of water and to a process for the determination of water using a solvent system which contains at least one higher alcohol as well as the customary Karl-Fischer solvents.

19 Claims, No Drawings

SOLVENT AND METHOD FOR THE KARL-FISCHER DETERMINATION OF WATER

The invention relates to a solvent for the Karl-Fischer determination of water and to a process for the determination of water, using a special solvent system.

BACKGROUND OF THE INVENTION

The determination of water by the Karl-Fischer method has been known for a long time (Angew. Chemie 48, 394 (1935)). In carrying out this method, a solvent is generally initially taken and, in order to remove the water content, is titrated to the end point with Karl-Fischer solution. A specific amount of the sample to be examined is then dissolved in the solvent and titrated with the Karl-Fischer solution until the end point is reached. The water content is then calculated from the amount of the sample, the consumption of Karl-Fischer solution and the factor of the solution.

The solvents employed are generally lower, monohydric alcohols, such as methanol and ethanol, or dihydric alcohols which are etherified on one side, such as ethylene glycol monomethyl ether. Examples of other solvents are pyridine, chloroform, dimethyl sulfoxide, formamide, dimethylformamide and other conventional solvents. The solvents are employed either on their own or as mixtures, in order to improve the solution properties for certain groups of substances or to suppress interfering side reactions.

However, the solubility of nonpolar compounds, such as petroleum fractions or diesel oils in these solvents is very poor. The problem is increased by the fact that these substances often contain very little water and it is therefore necessary to dissolve a fairly large amount of sample. Under these conditions, accurate determination of water by the Karl-Fischer method is not possible without the addition of a solubilizer. Previously, pyridine, halogenated hydrocarbons (for example chloroform), aromatic hydrocarbons (for example xylene) or aprotic solvents have been employed for this purpose, but none of these affords satisfactory results.

SUMMARY OF THE INVENTION

An object of the invention is to provide a solvent system which permits an accurate determination of water by the Karl-Fischer method. The method is particularly suitable in samples of nonpolar compounds.

Upon further study of the specification and appended claims, further objects and advantages of this invention will become apparent to those skilled in the art.

It has been found, surprisingly, that higher alcohols are much more suitable for this purpose than the solvents and solubilizers previously employed.

The invention relates to a solvent for the Karl-Fischer determination of water, which is characterized in that it contains at least one higher alcohol as well as the customary Karl-Fischer solvents.

The invention also relates to a process for the Karl-Fischer determination of water by means of this solvent.

Suitable higher alcohols are monohydric alcohols having 6 to 14 carbon atoms, preferably alcohols having 8 to 12 carbon atoms, such as octanol, nonanol, decanol, undecanol, dodecanol and isomers thereof. Decanol proves to be particularly suitable. These alcohols can be employed either on their own or as mixtures.

The solvent system according to the invention contains up to 70%, by volume preferably 20 to 50%, by volume of the higher alcohol according to the invention based on the total volume of the solvents per se (irrespective of other components). The remainder comprises customary Karl-Fischer solvents. Customary Karl-Fischer solvents include, but are not limited to, lower monohydric alcohols such as methanol and ethanol; dihydric alcohols which are etherified on one side, such as ethylene glycol monomethyl ether; pyridine, chloroform, dimethyl sulfoxide, formamide and dimethyl formamide. Other conventional solvents may be used. Particularly preferred are the lower alcohols. The solvent system is suitable for both coulometric and volumetric determinations of water by the Karl-Fischer method.

The solvent system is prepared by mixing, for example, methanol and decanol in a 1:1 ratio by volume. Water is determined by first titrating to the end point the solvent system according to the invention in which the sample to be determined is to be dissolved, adding the sample and again titrating to the end point with a conventional Karl-Fischer reagent.

A conventional Karl-Fischer reagent contains, for example, sulfur dioxide, iodine, and a base. Examples of suitable bases include pyridine or a pyridine substitute, such as imidazole, ethanolamines, morpholine, guanidine or other amine bases in a suitable solvent. Unless otherwise specified, all components are present in proportions which are well known in the art. Where not readily apparent, one of ordinary skill in the art could easily determine appropriate amounts of the conventional components. All amounts, conditions and procedures are well known in the art.

Without further elaboration, it is believed that one skilled in the art can, using the preceding description utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

EXAMPLE 1

Preparation of a Solvent

A solvent system is prepared by mixing 500 ml of anhydrous methanol and 500 ml of anhydrous decanol.

EXAMPLE 2

Coulometric Reagent

Composition:
136 g of imidazole,
64 g of sulfur dioxide and
12 g of imidazolium iodide, dissolved in 1 l of methanol.
Use:

The anode and cathode compartments of a 652 MET-ROHM Karl-Fischer coulometer are filled with the above solution of reagent and the instrument is brought into a ready state. Diesel oil is then injected until the solution becomes cloudy and the water values become incorrect. Not more than 2 ml are accepted.

The test is repeated with solutions in which 30% by volume of the reagent solution has been replaced by a solubilizer. The table below shows the solubilizer in each particular case and the maximum amount of diesel oil accepted.

| Solubilizer | Maximum acceptance |
| --- | --- |
| Chloroform | 6 ml |
| Xylene | 4 ml |
| Octanol | 10 ml |
| Decanol | 22 ml |
| Dodecanol | 17 ml |

The table shows that more than 5 times as much diesel oil can be dissolved with a solvent system containing decanol than with a solvent system containing xylene.

EXAMPLE 3

Volumetric Reagent

Composition:
158 g of diethanolamine and
96 g of sulfur dioxide dissolved in 1 l of methanol.
Use:
Diesel oil is added to 20 ml of the above reagent until cloudiness is formed. Maximum amount accepted: 0.3 ml.

The test is repeated with solutions in which 50% by volume of the reagent has been replaced by a solubilizer. The following table shows the solubilizer in each particular case and the maximum amount of diesel oil accepted.

| Solubilizer | Maximum acceptance |
| --- | --- |
| Chloroform | 8 ml |
| Xylene | 0.6 ml |
| Octanol | 9 ml |
| Decanol | 16 ml |
| Dodecanol | 17 ml |

In this case, compared with xylene, more than 26 times more diesel oil can be accepted in the solvent system with decanol.

EXAMPLE 4

A coulometric reagent is employed, analogously to Example 2, and the capacity to accept diesel oil is investigated using a homologous series of monohydric alcohols. The amount of reagent replaced is 30% by volume. The results are shown in the table below.

| Solubilizer | Maximum acceptance |
| --- | --- |
| Methanol | 2 ml |
| Ethanol | 4 ml |
| Propan-2-ol | 5 ml |
| n-Butanol | 9 ml |
| n-Pentanol | 12 ml |
| n-Hexanol | 14 ml |
| n-Octanol | 21 ml |
| n-Decanol | 28 ml |

EXAMPLE 5

A volumetric reagent is employed, analogously to Example 3, and the capacity to accept diesel oil is investigated using a homologous series of alcohols (in each case 50% by volume of the reagent is replaced). The results ae shown in the table below.

| Solubilizer | Maximum acceptance |
| --- | --- |
| Methanol | 0.2 ml |
| Ethanol | 1.2 ml |
| Propan-2-ol | 2.2 ml |
| n-Butanol | 5.4 ml |
| n-Pentanol | 9.2 ml |
| n-Hexanol | 15.6 ml |
| n-Octanol | 21.8 ml |
| n-Decanol | 19.2 ml |

A pronounced jump in the capacity of the solvent system to accept diesel oil can be noticed from hexanol onwards.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for determining the water content of a sample using a Karl-Fischer titration comprising conducting the Karl-Fischer titration using a Karl-Fischer solvent system containing at least one higher alcohol which is an aliphatic alcohol containing 8 to 12 carbon atoms.

2. The method of claim 1, wherein the at least one higher alcohol is octanol, nonanol, decanol, undecanol, dodecanol an isomer thereof or a mixture thereof.

3. The method of claim 2, wherein the at least one higher alcohol is decanol.

4. The method of claim 1, wherein the at least one higher alcohol is present in the solvent system in an amount of up to 70% by volume of the solvent system.

5. The method of claim 4, wherein the at least one higher alcohol is present in the solvent system in an amount of 20 to 50% by volume of the solvent system.

6. The method of claim 1, wherein the solvent system further comprises a lower alcohol.

7. The method of claim 6, wherein the lower alcohol is methanol or ethanol.

8. A method according to claim 1, wherein the sample is a nonpolar compound.

9. A method according to claim 8, wherein the sample is a petroleum fraction.

10. The method of claim 1, wherein the sample is a diesel oil.

11. The method of claim 1, wherein the solvent system further comprises pyridine.

12. A Karl-Fischer reagent comprising Karl-Fisher titration agents and a solvent therefor which comprises at least one higher alcohol which is an aliphatic alcohol having 8 to 12 carbon atoms.

13. The reagent of claim 12, wherein the at least one higher alcohol is present in the solvent in an amount of up to 70% by volume of the solvent.

14. The reagent of claim 12, wherein the at least one higher alcohol is present in the solvent in an amount of 20 to 50% by volume of the solvent.

15. The reagent of claim 12, wherein the solvent further comprises a lower alcohol.

16. The reagent of claim 15, wherein the lower alcohol is methanol or ethanol.

17. The reagent of claim 12, wherein the at least one higher alcohol is selected from the group consisting of octanol, nonanol, decanol, dodecanol and isomers thereof.

18. The reagent of claim 17, wherein the at least one higher alcohol is decanol.

19. The reagent of claim 12, wherein the solvent further comprises pyridine.

* * * * *